United States Patent [19]

Bak

[11] Patent Number: 4,879,789

[45] Date of Patent: Nov. 14, 1989

[54] MORTUARY DISPLAY PLATFORM

[76] Inventor: Donnell E. Bak, P.O. Box 443, Paradise, Calif. 95967

[21] Appl. No.: 205,649

[22] Filed: Jun. 13, 1988

[51] Int. Cl.$^4$ .............................................. A01N 1/00
[52] U.S. Cl. ............................................ 27/11; 27/2; 62/237
[58] Field of Search ...................... 27/2, 4, 5, 6, 7, 8, 27/11; 62/237, 176.6, 246, 458

[56] References Cited

U.S. PATENT DOCUMENTS

| | | | |
|---|---|---|---|
| 64,172 | 4/1867 | Waterman | 62/246 |
| 73,729 | 1/1868 | Kimball | 62/246 |
| 155,818 | 10/1874 | Weber | 27/11 |
| 205,102 | 6/1878 | Kinnaird | 62/458 |
| 2,973,631 | 3/1961 | Adkins | 62/246 |
| 3,257,820 | 6/1966 | Case et al. | 62/223 |
| 3,408,711 | 11/1968 | Paulivkonis | 27/6 |
| 3,435,494 | 4/1969 | Bernard | 27/11 |
| 3,488,818 | 1/1970 | Orr | 27/2 |
| 4,584,841 | 4/1986 | Guillaume | 62/62 |
| 4,773,230 | 9/1988 | Garrett | 27/11 X |

FOREIGN PATENT DOCUMENTS

| | | | |
|---|---|---|---|
| 1501246 | 10/1969 | Fed. Rep. of Germany | 62/246 U X |
| 2301259 | 5/1974 | Fed. Rep. of Germany | 27/11 U X |
| 8403500 | 11/1984 | Netherlands | 27/2 |

Primary Examiner—Robert A. Hafer
Assistant Examiner—Sam Rimell

[57] ABSTRACT

A mortuary display platform is provided with a transparent dome and refrigeration for viewing and for temporary preservation of a corpse prior to burial. A wheeled housing base containing a refrigeration unit, a dehumidifier, and a conditioned air control system supports the display platform. Electrical connections are included for electrical outlet operation. A rechargeable battery pack in the wheeled housing allows portable operation. The deceased can be viewed during services through the transparent dome, and conditioned air passed through vents inside the transparent dome from the conditioned air control system in the wheeled housing maintains the corpse in a cooled environment. An opaque burial cover fitting over the display platform encompassing the transparent dome is provided. The display platform can be detached from the wheeled housing base and, with the burial cover in place, the covered display platform can be use as a burial unit. Handles are provided along the sides of the upper section for carrying by pallbearers. The handles detach and are returned to the mortuary after the burial.

8 Claims, 3 Drawing Sheets

MORTUARY DISPLAY PLATFORM

BACKGROUND OF THE INVENTION

1. Field of the Invention:

This invention relates to mortuary display platforms and coffins in general. The present invention is particularly directed towards fully enclosed viewing platforms having glass or plastic transparent domes and self-contained refrigeration units designed for short term preservation of the deceased. The top platform section of the present invention also serves as a coffin and can be removed and fitted with a burial cover.

2. Description of the Prior Art:

A search was conducted to produce refrigerated coffins or caskets in the classes and sub-classes 27/1, 11, and 27. Patents deemed most pertinent to my invention included the following:

1. U.S. Pat. No. 3,257,820, was granted on June 28, 1966 to Case et al, for a cold storage container for cadavers. Case's container is designed primarily for shipping or transportation only and is not designed to serve as the burial coffin. Using this device as a burial coffin would prove cost prohibitive since the refrigeration system is contained inside the same housing as the cadaver and would be interned with the deceased. No provision is made in the design for viewing through a transparent cover.

2. On Nov. 5, 1968, Pauliukonis was issued U.S. Pat. No. 3,408,711, which discloses a cryoembalming casket. This device is also designed for cold storage of the cadaver over extended periods of time. The casket itself is separate from the refrigeration unit and contains no controlling means in the casket for reducing temperature. The refrigeration unit consists of a large cylinder which would again prove too expensive as well as too large to serve as the burial container. No means of viewing the deceased has been provided.

3. The Bernard patent, issued Apr. 1, 1969, U.S. Pat. No. 3,435,494, shows a coffin designed to replace oxygen inside the coffin with neutral gas, which reduces or prevents decomposition. No refrigeration means is provided nor is their a viewing area.

4. Weber was issued U.S. Pat. No. 155,818, on Oct. 13, 1874 for "Corpse-Coolers". This device utilizes ice for the cooling means which is ineffective in very hot conditions, requiring the addition of extra ice at certain intervals. Provisions must also be made for the water produced from the melting ice. The viewing area is also limited to the facial area.

5. U.S. Pat. No. 4,584,841, was granted to Guillaume et al., on Apr. 29, 1986, for an artificial hibernator and process for cold preservation of a human being. This device is not designed to be buried in the conventional manner but serves as a long term storage facility for the deceased.

For the health of the funeral workers and to promote or maintain an aesthetic appearance of the cadaver, undertakers have long practiced methods to prevent decomposition of the body. This practice is widely used and generally achieved by embalming. The increasing use of cremation as an alternative to the conventional burial system generally eliminates the use of embalming, however some form of preserving the body prior to cremation is still required. The use of refrigeration systems to preserve the deceased has been a convenient and effective method of preservation, but provides little or no means for allowing viewing of the body. These refrigeration units are also not designed as the burial containers and would either be cost prohibitive or too large to serve as such.

My invention effectively overcomes the previously mentioned disadvantages of the prior art by providing a viewing platform and burial unit along with a detachable refrigeration base unit. Odor and disease control is accomplished through refrigeration, closed air circulation, and a display platform which serves as a burial coffin without being opened. The novel and useful features of the present invention are not found in past art devices described in the issued patents or anticipated in the specifications and illustrations.

SUMMARY OF THE INVENTION

In practicing my invention, I have provided a mortuary display platform with the display platform as a top viewing section and a burial unit detachable from a wheeled base housing a refrigeration system. The display platform is covered by a transparent dome so the deceased can be viewed during services and is provided with an attachable opaque cover for use as a burial unit. The transparent dome covering the display platform is removable for placement of the cadaver on a mattress pad on the upper-facing display platform surface. With the transparent dome attached, the display platform serves as a viewing area for the body. Controlled refrigerated and dehumidified air is circulated by fan through vent openings one at each end of the display platform. Each air vent is affixed with a spring biased hinged door opened when the platform is attached to the wheeled refrigerator housing base, but which automatically swings closed as the platform is raised. A solid opaque covering fits over the transparent dome and the upper removable display platform becomes the burial coffin. Handles are provided along the sides of the display platform for carrying by pallbearers. The handles detach and are returned to the mortuary after the burial.

A complete refrigeration unit, a dehumidifier, and an air purification unit are housed in the wheeled housing base. Fans in the units circulate the processed air along ducts and through the viewing dome. A temperature sensor and a humidity sensor in the dome air path regulate the air flow and temperature inside the dome to a controlled condition. The wheeled housing base has an opening in the bottom to allow air circulation for cooling the housed electrical units. The temperature inside the viewing dome with the cadaver displayed is normally about 45 degrees fahrenheit but can be brought to 18 degrees fahrenheit should the condition of the corpse require it. The head end of the wheeled housing base is fitted with controls for operating the housed electrical equipment and operational dials indicate inside conditions. A rechargeable battery pack and an electrical cord for charging the batteries and for electrical outlet operation of the display platform is on a reel rolled up in a compartment for storage. The battery pack provides the mortuary display case and wheeled housing base with power to operate as a portable unit where required. Access to operational equipment is through the opened top of the wheeled housing base and through a compartment door in the foot end of the wheeled housing base.

Customarily, morticians provide family and friends viewing access to the deceased prior to burial, and this viewing time would be greatly limited if the body were not embalmed or preserved in some way. The present invention allows for extended viewing of the deceased maintained in a preserving environment. Transfer of the body from this unit is not necessary prior to burial, since a portion of the container itself serves as the casket. As the deceased is maintained refrigerated and in a sealed compartment during viewing and is buried in the same sealed compartment, odors and diseases are effectively controlled. The equipment of the present invention saves time, effort, and money for the mortician and should provide considerable savings in insurance and burial costs to remaining family members.

Therefore, it is a primary object of my invention to provide a mortuary display platform containing a refrigeration unit designed to preserve the cadaver prior to burial.

A further object of my invention is to provide a mortuary display platform which has a transparent dome for full length viewing of the body.

An even further object of my invention is to provide a mortuary display platform equipped with a detachable casket.

A still further object of my invention is to provide a mortuary display platform with controlled temperature, humidity, and purified air in a sealed viewing dome to effectively eliminate odors and for disease control.

Another object of my invention is to provide a refrigerated mortuary display platform which is portable.

Other objects and the many advantages of the present invention will be seen and understood by reading the specification and comparing numbered parts described with similarly numbered parts illustrated in the included drawings.

BRIEF DESCRIPTION OF THE DRAWINGS

FIG. 2A is an end view of the burial cover positioned over B, an end view of the display platform and the wheeled housing base showing electronic controls and dials in the head end panel of the wheeled housing base.

Figure 1:
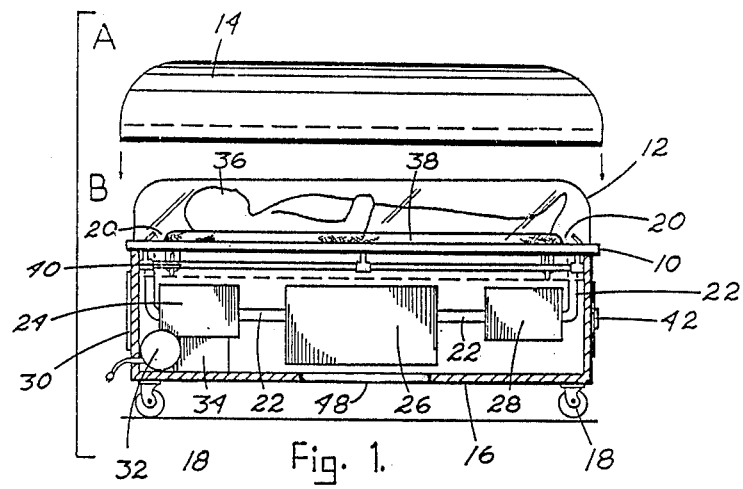
FIG. 1A is a side view of the opaque burial cover positioned over B, a side view of the display platform and the wheeled housing base. The wheeled housing base is sectioned to show the operational units housed inside.

DRAWING REFERENCE NUMBERS 10 display platform
12 transparent dome
14 burial cover
16 wheeled housing base
18 base wheels
20 air vents
22 air passage ducts
24 dehumidifier
26 refrigerator unit
28 air purifier
30 electronic controls
32 coiled electrical cord
34 rechargeable battery pack
36 cadaver
38 mattress pad
40 detachable handles
42 compartment door
44 turn locks
46 lock catches
48 opened bottom section
50 humidity sensor
52 temperature sensor
54 electrical connections
56 spring biased hinged vent doors
58 vertical rounded insert ends
60 air duct end insert shafts

DESCRIPTION OF THE PREFERRED EMBODIMENT

Figures 2, 3:
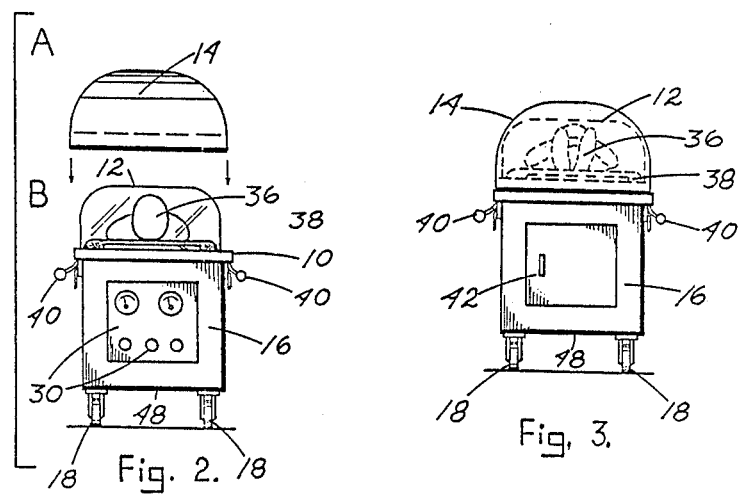
FIG. 3 is a view of the display platform and the wheeled housing base showing the opposite end from that of FIG. 2. The display platform has the burial cover attached and the storage compartment door in the foot end panel of the wheeled housing base is shown.
Figure 4:
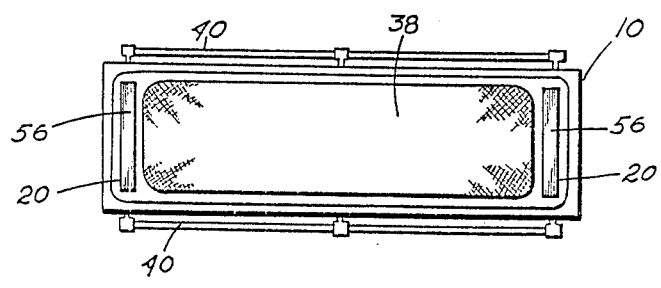
FIG. 4 is a top plan view of the empty display platform showing the mattress pad centrally positioned and the air passage vents one at each end. The grooved transparent dome track is shown in the upper surface edgewardly paralleling the display platform sides and ends. The detachable pallbearer handles are shown attached along both sides of the display platform.
Figure 5:
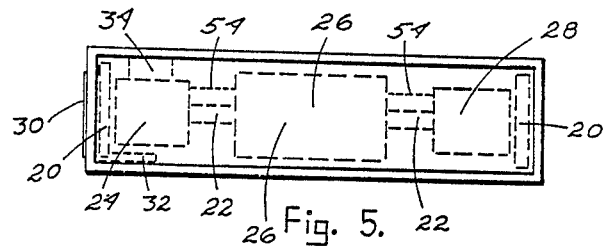
FIG. 5 is a top plan view of the wheeled housing base showing the opened top and having dotted lines indicating the refrigeration with associated mechanical and electrical equipment housed inside the wheeled housing base.
Figure 6:
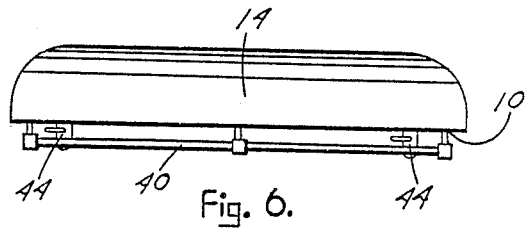
FIG. 6 is a side view of the detached display platform with the burial cover attached and locked in place. One of the two side pallbearer handles is illustrated.
Figure 7:
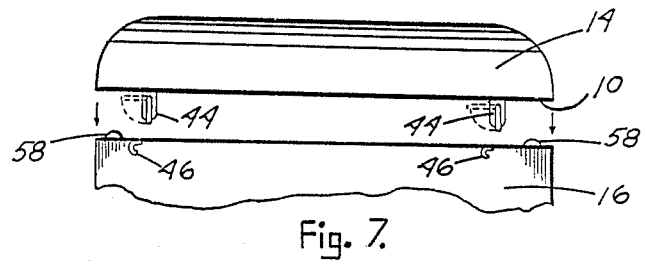
FIG. 7 is a side view of the display platform with burial cover attached and the handles removed. The lock arm hinging attachment of the display platform to the wheeled housing base is illustrated.
Figure 8:
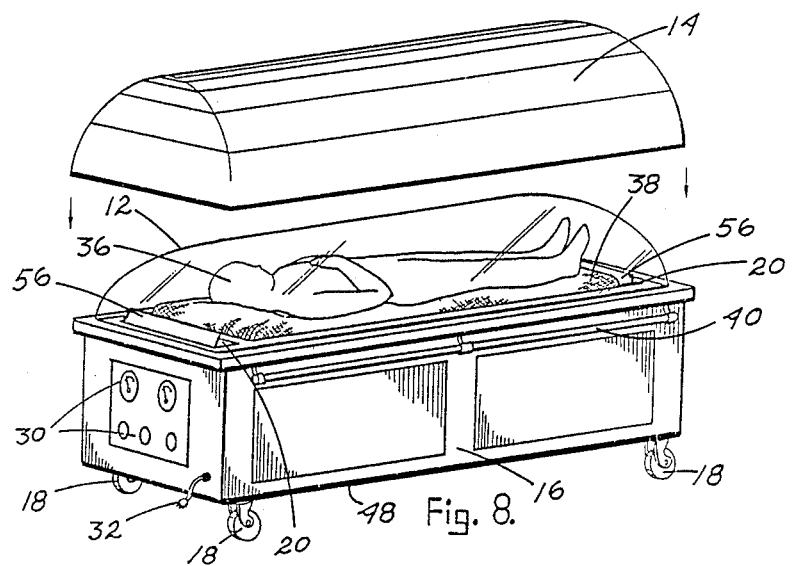
FIG. 8 is a perspective illustration of the device in use with the burial cover positioned above the display platform.
Figure 9:
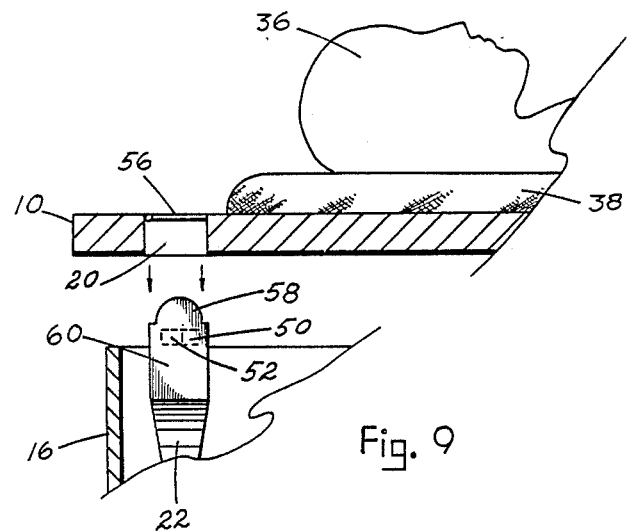
FIG. 9 is a sectional drawing showing one of the display platform air vents positioned above one of the air duct end insert and the rounded vertical insert ends which open the closed spring biased hinged vent door when the display platform is lowered onto the wheeled housing base.
Figure 10:
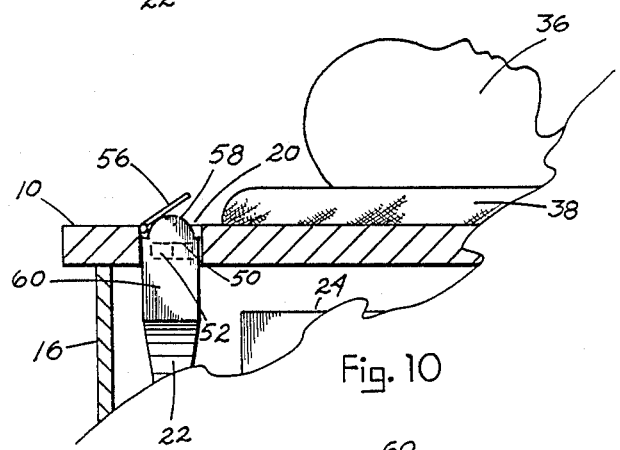
FIG. 10 is a sectional drawing showing the display platform lowered onto the wheeled housing base. The rounded vertical insert ends of the air duct end insert is shown positioned to maintain the spring biased hinge vent door of the display platform opened. Location of environmental control sensors is illustrated.
Figure 11:
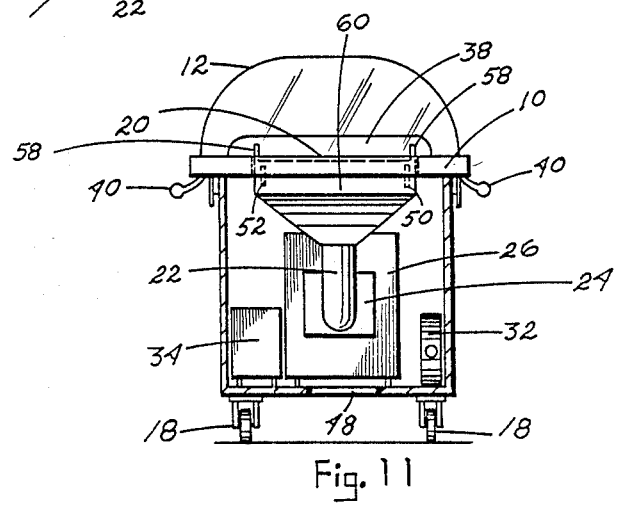
FIG. 11 is an enlarged end view of the display platform resting on the wheeled housing base. The wheeled housing base is sectioned to illustrate housed operational parts and vent connections between the air passage ducts in the wheeled housing base and the air vents at the ends of the display platform.

Referring now to the drawings at FIG. 1. where the display platform 10 is illustrated in operational position resting on wheeled housing base 16. A cadaver 36 lies on mattress pad 38 covered for viewing by transparent dome 12. Illustratively, opaque burial cover 14 is positioned above transparent dome 12. Base wheels 18 attached one each adjacent four lower corners under wheeled housing base 16 provide mobility and support wheeled housing base 16 a minimum of six inches above floor level. A refrigerator unit 26, a dehumidifier 24, and an air purifier 28 are connectively fitted by air passage ducts 22 and electrical connections 54 inside wheeled housing base 16. Humidity and air temperature inside transparent dome 12 circulating through air vents 20 at each end of display platform 10 is regulated by humidity sensor 50 and temperature sensor 52 affixed in the head end vent of air vents 20 as shown in FIG. 9 and FIG. 10. The electronic equipment is powered by coiled electrical cord 32 being plugged into an electrical outlet or in portable operation by rechargeable battery pack 34 (see FIG. 11). Electronic controls 30 in the head end panel of wheeled housing base 16 (see FIG. 2) sets the electrical operational modes. Rechargeable battery pack 34 in wheeled housing base 16 accessible through the opened top of wheeled housing base 16 (see FIG. 1 and FIG. 5) is automatically recharged when coiled electrical cord 32 is plugged into an electrical outlet. Rechargeable battery pack 34 supplies electrical power automatically for portable operation when electronic controls 30 are switch on and the plug of coiled electrical cord 32 is not plugged into an electrical outlet. Access to the inside of wheeled housing base 16 when display platform 10 is attached can be accomplished through compartment door 42 in the foot end of wheeled housing base 16 (see FIG. 3). To dissipate heat from the air conditioning system, wheeled housing base 16 has an opened center section in the bottom with the opening designated opened bottom 48 seen best in FIG. 11. Display platform 10 is locked onto wheeled housing base 16 by turn locks 44 fastened into lock catches 46. Display platform 10 can be unlocked and lifted free of wheeled housing base 16 and, with burial cover 14 locked on using the same turn locks 44 being fastened into lock catches 46 in burial cover 14, display platform 10 becomes the burial coffin for cadaver 36 (see FIG. 3, FIG. 4, and FIG. 5). Detachable handles 40 are provided along the sides of display platform 10 for carrying by pallbearers. Detachable handles 40 are removed just prior to internment and returned to the mortuary after the burial.

Transparent dome 12 is removable so cadaver 36 can be placed on mattress pad 38. The edges of transparent dome 12 fit a grooved retainer in the top of display platform 10. With transparent dome 12 in place, display platform 10 serves as a preserving compartment for cadaver 36 and a viewing platform during funeral services. Refrigerated air at a norm of 45 degrees fahrenheit to a low of 18 degrees fahrenheit is circulated from refrigerator unit 26 along air passage ducts 22 and into the domed chamber through air vents 20. The circulating air in air passage ducts 22 passes through air purifier 28 and dehumidifier 24. The humidity in the air and the temperature in transparent dome 12 is monitored and regulated by humidity sensor 50 and temperature sensor 52 in the head positioned vent of air vents 20. Circuitry to humidity sensor 50 and temperature sensor 52 can include extensions for placement of the sensors in various positions inside transparent dome 12. Air vents 20 are each affixed with spring biased hinged vent doors 56 which are forced open by vertical rounded insert ends 58 of air duct end insert shafts 60 when the display platform 10 is attached to wheeled housing base 16 (See FIG. 9 and FIG. 10). Spring biased hinged vent doors 56 automatically swing closed as the platform is raised.

Although I have described my invention in detail in the specification, it is to be understood that changes and modifications in the structure and design of the device may be practiced in so far as those changes and modifications do not exceed the scope of the appended claims.

The embodiments of the invention in which an exclusive property or privilege is claimed are defined as follows:

1. A refrigerated mortuary display platform comprising:

a display platform;

said display platform being a substantially rectangular panel having horizontal surfaces faced upwardly and downwardly, said panel being of sufficient thickness and size to support a human cadaver laid on said upwardly faced surface lengthwise on a rectangular mattress pad, there being end space and side space for venting and for attachment of coverings, there being detachable pallbearer handles fastened to the sides of said display platform, rectangularly there being shaped air passage vent openings cut through said display platform adjacent the ends thereof, said air passage vent openings covered by hinged vent doors spring biased to maintain a closed sealed position except when forced open from below by an opening means;

a transparent dome being primary of said coverings;

said transparent dome configured substantially rectangularly, opened downwardly, having upwardly rounded corners to form said dome, and structured of clear viable material in a size to encompass said cadaver, said mattress pad, and said air vents and form a controlled environmental cavity thereabout, there being and edge-aligned grooved track in said upwardly faced surface of said display platform sized to fit and retain said downwardly opened side of said transparent dome, the downwardly edge thereof;

a wheeled housing base;

said wheeled housing base being a box-like structure opened upwardly and downwardly and having an opened c section, said wheeled housing base being sized to join with and support said display platform, there being rubberized wheels pivotally affixed one each adjacent the four corners under said wheeled housing base providing mobility and supporting the downwardly side of said wheeled housing base a minimum of six inches above floor level, said wheeling base affixed with electrical powering means with operational circuitry, and controlling means with operational circuitry operating a refrigerator unit, a dehumidifier unit, and an air purifying unit connected by air ducts inwardly turned and upwardly widened into insert shafts fitting inside said air passage vent openings in said display platform providing air passage into said controlled environment cavity inside said transparent dome with said refrigerator unit, said dehumidifier unit, and said air purifying unit with said air duct connections affixed in operational alignment inside said wheeled housing base, there being connected in said controlling means monitoring means with automatic adjustment controls for maintaining set humidity and temperature levels in said transparent dome;

a burial cover being secondary of said coverings;

said burial cover opaque and of similar configuration to said transparent dome being sufficiently larger to encompass said transparent dome and having a downwardly opened side sized and shaped for the edges thereof to conform with and somewhat overlap in paralleling alignment the perimeter edging of said display platform, there being means for fastened said burial cover to said display platform with edge to edge alignment, the assemblage of said burial cover and said display platform with said display platform removed from said wheeled housing base providing a unitary burial container.

2. The device of claim 1 wherein said opening means for said spring biased hinged vent doors in said display platform includes vertically rounded end sections of said air ducts inwardly turned and upwardly and widened into end insert shafts with said end inserts shafts sized to position upwardly inside said air passage vents and maintain said spring biased hinge vent doors in an opened position only when said display platform rests atop said wheeled housing base.

3. The device of claim 1 wherein said electrical powering means includes in said operational circuitry an electrical attachment cord affixed in said wheeled housing base on a reel with said electrical attachment cord fitted with a plug compatible with standard electrical outlets.

4. The device of claim 1 wherein said electrical controlling means includes in said operational circuitry electrical controls with exterior manual operational access and visible condition response dials in an end panel of said wheeled housing base, with said electrical controls being operational mode setting devices for instituting said controlled environment in said cavity under said transparent dome.

5. The device of claim 1 wherein said electrical controlling means includes in said operational circuitry a humidity sensor and a temperature sensor affixed in the air path effecting said controlled environment in said transparent dome with said sensors both automatically responsive to environmental changes and circuited to adjust air input condition to maintain said controlled environment at a preset level.

6. The device of claim 1 wherein said opaque burial cover is manufactured of nontransparent materials or combinations of materials of sufficient impregnability to withstand ground interment with suitable materials for the purpose including metals and plastics.

7. The device of claim 1 wherein said display platform and said wheeled housing base are manufactured of suitable materials including wood, metal steel, and plastics.

8. The device of claim 1 wherein said transparent dome is structured of clear viable material, clear viable material including glass and clear plastics.

* * * * *